United States Patent [19]

Reierson et al.

[11] Patent Number: 4,501,679
[45] Date of Patent: Feb. 26, 1985

[54] BICYCLIC AMIDE KETAL DERIVATIVES

[75] Inventors: Robert L. Reierson; Hugh F. Hussey; Edmund P. Woo, all of Midland, Mich.

[73] Assignee: The Dow Chemical Company, Midland, Mich.

[21] Appl. No.: 582,104

[22] Filed: Feb. 21, 1984

Related U.S. Application Data

[63] Continuation-in-part of Ser. No. 441,346, Nov. 15, 1982, abandoned.

[51] Int. Cl.³ .............................................. C10M 1/32
[52] U.S. Cl. ................................ 252/77; 252/51.5 R; 252/392; 548/218
[58] Field of Search ................... 252/51.5 R, 77, 392; 548/218

[56] References Cited

U.S. PATENT DOCUMENTS

| | | | |
|---|---|---|---|
| 3,507,830 | 4/1970 | Feinauer | 528/190 |
| 3,600,214 | 8/1971 | Feinauer et al. | 8/598 |
| 3,640,957 | 2/1972 | Tomalia et al. | 528/117 |
| 4,277,353 | 7/1981 | Deen et al. | 252/77 |
| 4,277,354 | 7/1981 | Brois et al. | 252/77 |
| 4,320,024 | 3/1982 | Reierson et al. | 252/77 |

FOREIGN PATENT DOCUMENTS

| | | |
|---|---|---|
| 2344607 | 3/1975 | Fed. Rep. of Germany ...... 548/218 |
| 3143251 | 5/1983 | Fed. Rep. of Germany . |
| 1518386 | 3/1968 | France . |

OTHER PUBLICATIONS

Burzin et al., "4,8-Dioxa-1-azabicyclo[3.3.0] octane from iminodiethanols and nitriles", Angew. Chem., 1973, 85(23), 1055–6, (CA 81:25594).

Feinauer et al., "Addition of epoxides to cyclic imino esters", Justus Leibigs Ann. Chem. 698, 174–9, (1966), (CA 66:37857).

Primary Examiner—Paul Lieberman
Assistant Examiner—Robert A. Wax
Attorney, Agent, or Firm—Douglas N. Deline

[57] ABSTRACT

Bicyclic amide ketals such as 1-aza-4,6-dioxabicyclo[3.3.0]octanes have utility as water or acid scavengers for addition to functional fluids.

16 Claims, No Drawings

4,501,679

BICYCLIC AMIDE KETAL DERIVATIVES

CROSS-REFERENCE TO RELATED APPLICATION

This is a continuation-in-part of application Ser. No. 441,346, filed Nov. 15, 1982, now abandoned.

BACKGROUND OF THE INVENTION

The present invention relates to certain bicyclic amide ketals and derivatives thereof, which have been found to be useful additives for inclusion in functional fluids particularly hydraulic fluids as acid and water scavengers. The present invention also includes as one embodiment thereof certain of these bicyclic amide ketals containing hetero atom functionality that were previously known.

In U.S. Pat. No. 4,277,354 to Brois et al., certain oil-soluble 2- and/or 8-alkyl-substituted 1-aza-3,7-dioxabicyclo[3.3.0]oct-5-yl methyl alcohols are disclosed that have particular utility as additives to functional fluids to prevent corrosion of copper. Ester derivatives thereof of related structure are disclosed in U.S. Pat. No. 4,017,406. Further alkylene glycol esters of these compounds are disclosed in U.S. Pat. No. 4,199,463.

In U.S. Pat. No. 3,600,214 to Feinauer et al., certain 5-alkyl- or 5-aryl-4,6-dioxa-1-azabicyclo[3.3.0]octanes having utility as dyeing aids for synthetic fibers are disclosed.

Functional fluids are often exposed to extreme operating conditions. Such fluids may have to withstand elevated temperatures or be subjected to alternating extremes of high and low temperatures while maintaining desirable fluid properties. In addition, many fluids are exposed to sources of chemical contamination. Especially detrimental may be acid contaminants and water, either of which may seriously degrade fluid performance or affect additional components in the fluid system causing corrosion or degradation of system parts and ultimately contribute to a failure of the fluid system. Even where structural failure may not be a problem, contamination may still be undesirable. For example, in a dielectric fluid, small quantities of water on the order of only a few parts per thousand may seriously degrade the fluids dielectric properties.

Accordingly, it is well-recognized that nonaqueous functional fluids may require the presence of additives to modify or control the effects of contaminants, particularly water and acids, therein. Although numerous additives are currently known and employed, a continued need exists to provide new additives that are compatible with many varieties of fluids or to provide improved protection under various operating conditions.

SUMMARY OF THE INVENTION

According to the present invention it has now been found that functional fluids may be protected from the adverse effects of water or acid contamination by addition thereto of an amount that is effective to reduce water or acid buildup therein of a bicylic amide ketal compound corresponding to the formula:

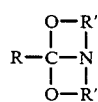

wherein R is hydrogen or a substituent of up to 20 carbons selected from the group consisting of alkyl, aryl and inertly-substituted derivatives thereof, and R' each occurrence independently is a $C_{2-3}$ alkylene moiety optionally substituted with up to 4 R" groups where R" is a substituent of up to 10 carbons selected from the group consisting of alkyl, aryl, and inertly substituted derivatives thereof. By the term "inert" is meant substituents that do not react to form interfering products during use in functional fluids and that do not interfere with preparation or purification of such compounds.

The ability of the above compounds to prevent adverse effects caused by the presence of water or acids is believed to be due to their unique reactivity owing to the chemical structure thereof. The present compounds are capable of preparing hydrolysis products that remain uniquely compatible with the functional fluid instead of forming insoluble or volatile reaction products. As a further advantage, the compositions may be easily modified so as to alter the reactivity thereof thereby modifying the ability of the compounds to maintain extremely low water or acid levels in the functional fluid. As an example, extremely reactive compounds may reduce the water content of a fluid to levels such that increased uptake of moisture results upon exposure to atmospheric or other moisture sources, thereby resulting in rapid depletion of the water scavenger. Accordingly, fluids that are unlikely to come in contact with sources of moisture or acids during their lifetimes, such as dielectric fluids that are encapsulated in electrical devices, may well benefit from the use of highly reactive water scavengers. On the other hand, fluids that must bear continual exposure to humidified air or other sources of moisture, such as hydraulic brake fluids, would do well to employ less reactive compounds. Generally, the presence of substituents on the $C_{2-3}$ alkylene moieties (R') forming the rings of bicylic amide ketals tend to reduce the reactivity of the present compounds.

Certain of the above-defined compositions are also novel compositions of matter. Accordingly, the present invention additionally includes as one embodiment thereof novel bicyclic amide ketal derivatives corresponding to the formula:

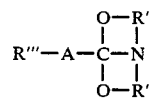

wherein:
R''' is a nitrile, acetal or ketal group;
A is $C_{2-10}$ alkylene; and
R' is as previously defined.

These novel compounds have been found to be especially suited as additives to hydraulic fluids and other functional fluids, e.g., lubricants, dielectric fluids, cutting fluids, heat transfer fluids, etc., in order to scavenge water and acids.

DETAILED DESCRIPTION OF THE INVENTION

Functional fluids, particularly hydraulic fluids have been called upon to face ever more demanding service requirements in recent years. In particular, there is an increased need for hydraulic fluids that retain a long service life, as long as 10 years or more, with little or no degradation of performance. One standard generally required of modern hydraulic fluids is a wet boiling point, e.g., the boiling point of a humidified sample, of at least 356° F. (180° C.) over the practical life of the system, e.g., 10 years. Other criteria must also be met by the fluid, such as rubber compatibility, fluidity at lowered temperatures, low toxicity, noncorrosivity to metals, pH, lubricity, etc.

Several recently developed modern hydraulic fluids have achieved satisfactory performance in many of the above areas. In particular, such fluids include cyano derivatives of cyclic ketals and acetals disclosed in U.S. Pat. No. 4,320,024 to R. L. Reierson et al. Additional examples include the well-known silicon-containing fluids such as poly(dialkylsiloxane) fluids and fluids comprised of diesters of polyglycol ethers, phosphate ester fluids, etc. In many of these and other high performance hydraulic fluids it has been discovered that a water compatibility agent or scavenger may be required in order to maintain desirable high wet boiling points for the above-mentioned time period.

In this regard, it is desirable that both the active scavenging agent and its hydrolysis products be soluble and otherwise nonreactive with remaining components of the hydraulic fluid and with additional components of commercial hydraulic fluids that may accidently be mixed with or added to the hydraulic system during its service life. Additionally, the scavenger and its reaction products should not upset the delicate balance of fluid properties and in particular, should be noncorrosive to the various metals such as iron, zinc, aluminum, brass and steel used in braking and other hydraulic systems, and maintain fluid viscosity, rubber compatibility, pH, lubricity and boiling points within specifications. Finally, the scavenger must be sufficiently and selectively reactive with water under typical brake fluid conditions of pH 7.0–11.5 in the presence, possibly, of amine and hydroxyl functional additives or components, that the water content of the fluid will be maintained sufficiently low to prevent boiling point degradation. At the same time, however, it is preferable that the fluid not be completely desiccated so as to enhance the rate of further absorption of moisture thereby more rapidly depleting the scavenger. Furthermore, it is desirable that the hydrolysis products not reversibly dehydrate thereby reforming the scavenger and water, particularly at elevated temperatures where the need for protection against vapor formation is greatest. In addition, the scavenger and hydrolysis products must possess good thermal stability in order that they not degrade the fluid qualities upon exposure to elevated temperatures over prolonged time periods.

Upon hydrolysis, the compounds employed in the present invention form one or two different products, a hydroxyalkylamide or an aminoalkyl ester. The pH of the reaction determines the predominant product formed. The hydrolysis is illustrated schematically as follows:

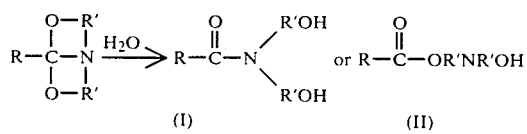

(I) (II)

In the presence of acid, the hydroxyalkylamino alkyl ester (II) is rapidly formed as the principal reaction product. Isomeric products may be prepared depending on the ether position at which acid cleavage occurs. Because amine functionality present in the acid hydrolysis product (II) may neutralize additional acid functionality, the present invented compounds are uniquely capable and effective acid scavengers for both strong and weak acids. When acid is not present, the principal hydrolysis reaction product is the di(hydroxyalkyl)-substituted amide (I).

In the compositions, inert substituents on R″ or on R include nitrile, acetal, ketal, hydroxy, alkoxy, aryloxy, hydroxyalkyl, and hydroxy- or alkoxy-terminated (poly)alkyleneoxy.

More particularly, acetal or ketal substituents correspond to the formula:

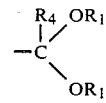

wherein $R_4$ is a $C_{1-10}$ group selected from alkyl and alkyl-terminated (poly)alkyleneoxy and each $R_1$ independently is $-CHR_2CH_2O-_nR_3$, were $R_2$ is hydrogen, methyl, or ethyl, $R_3$ is $C_{1-10}$ alkyl and n is a number greater than or equal to zero, or both $R_1$'s may be joined together to form a $C_2$ or $C_3$ alkylene group.

Preferred bicyclic amide ketal derivatives are 1-aza-4,6-dioxabicyclo[3.3.0]octane derivatives corresponding to the formula:

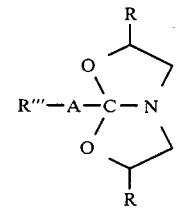

wherein R‴, A and R are as previously defined.

Highly preferred 1-aza-4,6-dioxabicyclo[3.3.0]octane derivatives are those wherein one or both of R are hydrogen or $C_{1-4}$ alkyl, most preferably methyl, and A is $C_2-C_4$ alkylene or $C_{1-4}$ alkyl-substituted derivatives thereof. Examples of suitable compounds are 5-(2-cyanobutyl)-3,7-dimethyl-1-aza-4,6-dioxabicyclo[3.3.0]octane; 5-(3-cyanobutyl)-3,7-dimethyl-1-aza-4,6-dioxabicyclo[3.3.0]octane; 5-(4-cyanobutyl)-3,7-dimethyl-1-aza-4,6-dioxabicyclo[3.3.0]octane; 5-(2-cyanobutyl)-3-methyl-1-aza-4,6-dioxabicyclo[3.3.0]octane; 5-(3-cyanobutyl)-3-methyl-1-aza-4,6-dioxabicyclo[3.3.0]octane; 5-(4-cyanobutyl)-3-methyl-1-aza-4,6-dioxabicyclo[3.3.0]octane; 5-(3,3-dimethoxypropyl)-3,7-dimethyl-1-aza-4,6-dioxabicyclo[3.3.0]octane; 5-(3,3-dimethoxypropyl)-3-methyl-1-aza-4,6-dioxabicyclo[3.3.0]octane; 5-(2-(1,3-dioxolanyl)ethyl)-3,7-dimethyl-1-aza-4,6-dioxabicyclo[3.3.0]octane; 5-(2-(1,3-dioxolanyl)ethyl)-3-methyl-1-aza-4,6-dioxabicyclo[3.3.0 octane; etc.

The compounds employed according to the present invention may be prepared according to known techniques. For example, R. Feinauer, *Synthesis*, 1, 16 (1971), described the reaction of oxazolines with epoxides to prepare 4,6-dioxabicyclo[3.3.0]octanes. The process may be used to react substituted oxazolines according to the following schematic illustration:

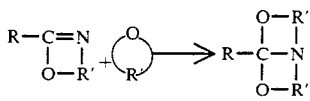

wherein R and R' are as previously defined.

An alternative procedure adapted from that disclosed by the same reference and in addition by Burzin and Feinauer, *Angew. Chemie*, 85, 1055 (1973) and DE 2,344,607, involves the reaction of a dialkanolamine with an amide acetal, amide thioacetal or nitrile. The procedure is illustrated as follows:

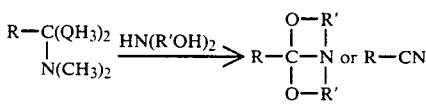

where Q is an oxygen or sulfur moiety and R, and R' are as previously defined.

It has additionally been discovered that in place of the above-described amide acetals, amide thioacetals or nitriles, it is possible to employ the corresponding bis(-hydroxyalkyl)amide which under conditions of elevated temperature and reduced pressure has been found to dehydrate to form the desired bicyclic compound. The bis(hydroxyalkyl)amides may be prepared by the known reaction of a di(hydroxyalkyl)amine and an acid chloride, ester or anhydride. The procedure is illustrated by the following schematic diagram:

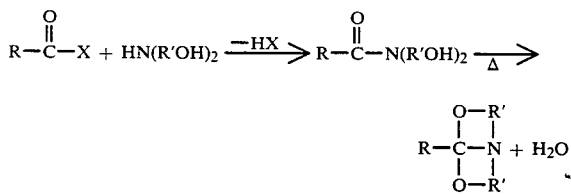

wherein X is the remnant of the acid chloride, ester or anhydride and R and R' are as previously defined.

The use of reduced pressure is important to the success of this method of preparation. The skilled artisan will note that while in service, the desired hydrolysis reaction to remove water is the reverse of the above process. However, at other than reduced pressures, the above hydrolysis products are highly resistant to dehydration.

The compounds of the invention may be employed as additives to wide variety of functional fluids. Examples include hydraulic fluids, especially aprotic fluids, comprised of nitrile functional acetals or ketals (disclosed, for example, in previously identified U.S. Pat. No. 4,320,024); esters of mono, di- or polycarboxylic acids; esters of carbonic or phosphoric acids; (poly)alkylene glycols, glycol ethers or formal derivatives thereof; (poly)alkylene glycol diethers; and silicone fluids including siloxanes, polysiloxanes, etc.

Additional examples of functional fluids for use according to the present invention include lubricating oils such as mineral oils and synthetic oils, heat-transfer fluids, automatic transmission and other traction fluids, dielectric fluids, cutting fluids and the like.

Additional components of hydraulic fluids for use in combination with compounds according to the present invention are those known and used in conventional hydraulic fluids and disclosed, for example, in the above-identified U.S. Pat. No. 4,320,024.

The bicyclic amide ketals are employed in minor or major proportions, depending on the application intended for the resulting fluid and the desired degree of protection from water or acid contamination. Suitably from about 1 percent to about 90 percent by weight of the previously defined compounds may be added. Preferred are amounts from about 1.5 percent to 50 percent by weight and most preferred are amounts from about 2 percent to 25 percent by weight.

The bicyclic amide ketals derivatives are blended with the additional components of the functional fluid in any manner, and may be added as part of an inhibitor package to newly formulated or existing functional fluids while in service.

SPECIFIC EMBODIMENTS

Having described the invention, the following examples are provided as further illustrative and are not to be construed as limiting.

EXAMPLE 1

5-(3-cyanobutyl)-3,7-dimethyl-1-aza-4,6-dioxabicyclo[3.3.0]octane

Di(2-hydroxy-1-propyl)amine (2070 g) is weighed into a 5000-ml 5-necked round-bottom flask equipped with a thermowell, overhead stirrer, glycol bubbler capped reflux condenser, pressure equalizing addition funnel, and needle by which means gas may be added to the liquor. The diisopropanolamine is melted under argon atmosphere and metallic sodium (7 g) is added. Stirring is continued with heating to 100° C. to react and dissolve the sodium (about 45 min.). A commercially available mixture (1622 g) comprising 1,3-dicyanobutane (80-85 percent) and remainder comprising essentially 1,2-dicyanobutane is added dropwise over a 4½-hour interval after which time the temperature is increased to 125° C.–130° C. while a gentle stream of argon is employed to sweep out ammonia.

The reaction is followed by gas phase chromatography and terminated after 21 hours by neutralization with ethaneoic acid (18 g). The crude product is carefully distilled under vacuum through a 25×250 mm vacuum jacketed Vigreaux column to yield 1226 g of >99 percent pure product, with a boiling point of 110° C.–113° C. at 0.1 torr (13.3 Pa). Characterization by nuclear magnetic resonance spectroscopy, infrared spectroscopy and mass spectrometry shows the product to be primarily 5-(3-cyanobutyl)-3,7-dimethyl-1-aza-4,6-dioxabicyclo[3.3.0]octane along with minor amounts of the 5-(2-cyanobutyl)isomer.

EXAMPLE 2

Hydrolysis

The product prepared in Example 1 is dissolved in acetonitrile and combined with an equimolar amount of distilled water at room temperature and stirred by magnetic bar. The progress of the conversion from the amide ketal to the amide and ester products is followed qualitatively by infrared spectroscopy. In the presence of 0.54 weight percent monoisopropanolamine, a common brake fluid corrosion inhibitor and pH control additive, both amide (1620–1640 cm$^{-1}$) and ester (1720–1730 cm$^{-1}$) bands appear within the first hour after the water addition. The amide band continues to increase but the ester band decreases as the reaction continues.

EXAMPLE 3

Acid Hydrolysis

An additional amount of the reaction product prepared according to Example 1 is combined with an equimolar amount of water as concentrated hydrochloric acid (30 mole percent hydrogen chloride) and stirred. During the addition, the pH of the resulting solution does not decrease below about 6.5. Analysis of the resulting mixture by infrared absorbance spectroscopy indicates the primary reaction products are the corresponding esters as evidenced by a broad absorption band at 1720–1730 cm$^{-1}$.

EXAMPLE 4

Inherent Corrosion

A further sample of the reaction product prepared according to Example 1 is humidified according to the procedure outlined in Federal Motor Vehicle Safety Standard No. 116, 49 CFR §511.116 (1971). The sample together with an additional unhumidified sample is tested for corrosion substantially according to the procedure of 49 CFR §511.116. No water is added to the samples other than by humidification. Weight loss in g/cm$^2$ is measured. Results are contained in Table I.

TABLE I

| | Metal Strip Weight Change (g/cm$^2$) | | | | | |
|---|---|---|---|---|---|---|
| | Tinned Iron | Mild Steel | Aluminum | Cast Iron | Brass | Copper |
| [1]HS | −0.1 | 0.0 | 0.0 | 0.0 | 0.0 | −0.1 |
| [2]UHS | −0.1 | 0.0 | 0.0 | 0.0 | −0.1 | −0.2 |

TABLE I-continued

| | Metal Strip Weight Change (g/cm$^2$) | | | | | |
|---|---|---|---|---|---|---|
| | Tinned Iron | Mild Steel | Aluminum | Cast Iron | Brass | Copper |
| [3]FMVSS | ±0.2 | ±0.2 | ±0.1 | ±0.2 | ±0.4 | ±0.4 |

[1]Humidified Sample
[2]Unhumidified Sample
[3]FMVSS No. 116 maximum weight change specification

EXAMPLES 5–10

Bicyclic amide ketals further identified in Table II are prepared in 30 percent weight solutions using 1,3-dioxolane-2-butanenitrile diluent. The solutions are tested for hydraulic fluid properties substantially according to Federal Motor Vehicle Safety Standard No. 116, 49 CFR §511.116. Results are contained in Table II.

TABLE II

| Example | Compound[a] | Purity (% by VPC[b]) | ERBP (°C.)[c] dry | ERBP (°C.)[c] wet | % H$_2$O | pH | Viscosity (cst −40° C.) dry | Viscosity (cst −40° C.) wet | Rubber Brake Cup Change in Diameter (mm) | Rubber Brake Cup Change in Hardness (IRHD) |
|---|---|---|---|---|---|---|---|---|---|---|
| 5 | NCCH(CH$_3$)CH$_2$CH$_2$—Z | 99.0 | 244 | 225 | 0.69 | — | — | 1268 | 1.1 | −6 |
| 6 | NCCH(CH$_3$)CH$_2$CH$_2$—Y | 98.0 | — | 200 | 0.85 | — | — | — | — | — |
| 7 | NCCH$_2$CH$_2$CH$_2$CH$_2$—Z | 95.0 | — | 200 | 0.93 | — | — | 2631 | — | — |
| 8 | CH(OCH$_3$)$_2$CH$_2$CH$_2$—Z | 98.0 | — | 205 | 0.87 | 9.87 | — | 1542 | — | — |
| 9 | OCH$_2$CH$_2$OCHCH$_2$CH$_2$—Z | 99.5 | — | 230 | 0.57 | 9.75 | 419 | 1324 | 1.5 | −9 |
| 10[d] | diluent only | 99.5 | 233 | 175 | 1.45 | — | — | 83 | 0.8 | −8 |
| | DOT 4 Specification | — | 230 | 155 | — | 7.0–11.5 | 1800 | — | 0.15–1.4 | −15–0 |
| | DOT 5 Specification | — | 260 | 180 | — | 7.0–11.5 | 900 | — | 0.15–1.4 | −15–0 |

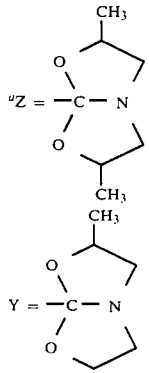

[a]
$$Z = \begin{array}{c}\text{structure with } CH_3 \text{ group}\end{array}$$

$$Y = \begin{array}{c}\text{structure with } CH_3 \text{ groups}\end{array}$$

[b]vapor phase chromatography
[c]equilibrium reflux boiling point
[d]diluent, NCCH$_2$CH$_2$CHOCH$_2$CH$_2$O (with bracket indicating ring)

The results of Table II indicate that in addition to providing protection against water or acid contamination, the named bicyclic amide ketal derivatives are highly suited for use in hydraulic fluids due to the high wet equilibrium reflux boiling points obtainable through their use and by the relatively low effect on rubber swelling attributable thereto.

EXAMPLE 11

A sample hydraulic fluid base formulation (lacking a corrosion inhibitor, antioxidant, and other special additives) is prepared comprising the following listed components in the indicated weight percentages.

2-(2-cyanoethyl)-1,3-dioxolane—50%
2-(2-cyanoethyl)-4-methyl-1,3-dioxolane—13%
5-(3-cyanobutyl)-3,7-dimethyl-1-aza-4,6-dioxabicyclo[3.3.0]octane—20%
bis(2-(2-(2-methoxyethoxy)ethoxy)ethyl)pentanedioate (CH$_2$—CH$_2$COO—CH$_2$CH$_2$O—$_3$CH$_3$]$_2$)—17%

The hydraulic base fluid is tested substantially according to the procedures of FMVSS No. 116. Results are contained in Table III.

TABLE III

| Test | Result | DOT 5 Specification |
|---|---|---|
| Dry Eq. Reflux B.P. °C. | 242 | ≧260 |
| Wet Eq. Reflux B.P. °C. | 200 | ≧180 |
| (water %) | (0.93) | |
| Viscosity (cst) | | |
| 100° C. (dry) | 1.5 | ≧1.5 |
| 50° C. (dry) | 3.7 | — |
| −40° C. (dry) | 697 | ≦900 |
| −40° C. (wet) | 1750 | — |
| pH | 8.4 | — |
| High Temp. Stability Δ °C. | +1 | ±3.0 max |
| Chemical Stability Δ °C. | +2 | — |
| Corrosion (avg. of 2 tests, humidified) | | |
| final pH | 8.0 | — |
| Sediment (vol. %) | 0.001 | ≦0.1 |
| Rubber Cup | | |
| base diameter (mm) | +0.58 | 0.15-1.4 |
| hardness (IRHD) | −5 | 0 to −15 |
| max. metal wt. change (mg/cm²) | | |
| tinned iron | 0.0 | 0.2 |
| mild steel | 0.0 | 0.2 |
| aluminum | 0.0 | 0.1 |
| cast iron | 0.0 | 0.2 |
| brass | 0.4 | 0.4 |
| copper | 0.4 | 0.4 |
| Fluidity (bubble flow, sec.) | | |
| after 144 hr @ −40° C. | 1.0 | ≦10.0 |
| after 6 hr @ −50° C. | 3.3 | ≦35.0 |
| Evaporation wt. loss % | | |
| Residue after 168 hr @ 100° C. open dish | 65 | ≦80.0 |
| Residue Fluidity @ −5° C. 5 mm flow time (sec) | 0.9 | ≦5.0 |
| Water tolerance (humidified sample) | | |
| bubble flow time (sec) after 120 hr @ −40° C. | 3.8 | ≦10.0 |
| sedimentation (vol. %) after 24 hr @ +60° C. | <0.001 | ≦0.15 |
| Compatibility with SAE RM-1 after 24 hr @ 60° C. | | |
| sedimentation | <0.001 | ≦0.05 |
| appearance | Excellent | |
| Oxidation Resistance (56.11) Metal wt. loss (mg/cm²) | | |
| aluminum | 0.000 | ≦0.05 |
| cast iron | +0.018 | ≦0.3 |
| Rubber Cup (56.12) | | |
| 72 hr @ 70° C. | | |
| Δ base diameter (mm) | +1.02 | 0.15-1.4 |
| Δ hardness (IRHD) | −6.0 | 0 to −15 |
| 72 hr @ 120° C. | | |
| Δ base diameter (mm) | 1.17 | 0.15-1.4 |
| Δ hardness (IRHD) | −8.0 | 0 to −15 |
| Stroking | pass | |

It is seen by the results of this testing that a hydraulic fluid having excellent physical properites and long-term resistance to the effects of water can be prepared employing as one ingredient the named bicyclic amide ketal compounds. Even in the absence of corrosion and oxidation inhibitors, the fluid meets or exceeds the requirements of FMVSS No. 116 excepting in dry equilibrium reflux boiling point. In addition, it is highly flowable even under extreme conditions of use.

EXAMPLE 12

Additional bicyclic amide ketals are prepared for testing of compatibility in various functional fluids. Accordingly, an alkyl-substituted compound, 3,7-dimethyl-5-propyl-1-aza-4,6-dioxabicyclo[3.3.0]octane, is prepared by reaction of diisopropylamine and 1-butane nitrile acccording to the procedure of Example 1. The product is isolated and purified by distillation. Two test formulations are prepared by combining the compound with bis(2-(2-(2-methoxyethoxy)ethoxy)ethyl)pentanedioate (CH$_2$—CH$_2$C(O)O(CH$_2$CH$_2$O)$_3$—CH$_3$]$_2$) and tributylphosphate (Phosflex ®4, available from Stauffer Chemical Company). The formulations contain 20 percent by weight of the bicyclic amide ketal. The test formulations as well as an unprotected sample of each dicarboxylic ester and phosphate ester base fluid are humidified by the method described in FMVSS No. 116 excepting that the period for humidification was extended by 26 hours (93 hours total). The samples are heated to reflux temperature and the reflux boiling points (wet) determined. Results are contained in Table IV.

TABLE IV

| Fluid | Boiling Point | |
|---|---|---|
| | °F. | (°C.) |
| dicarboxylic ester + scavenger | 360 | (182) |
| control | 294 | (146) |
| tributylphosphate + scavenger | 325 | (163) |
| control | 285 | (141) |

In both examples, it is seen that an increase in wet boiling point is observed by use of the compounds of the present invention indicating that fluid properties may be protected from adverse effects due to the presence of water by use of the present invention. No precipitate or deposit was observed after completion of the tests. This example further illustrates that the water and acid scavengers of the present invention may suitably be combined with a wide variety of commonly available functional fluids.

What is claimed is:

1. A compound corresponding to the formula:

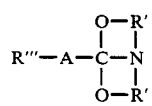

wherein:
R′′′ is a nitrile, acetal, or ketal group;
A is C$_{2-10}$ alkylene; and
R′ each occurrence independently is a C$_{2-3}$ alkylene moiety optionally substituted with up to 4 R′′ groups wherein R′′ is a substituent of up to 10 carbons selected from the group consisting of alkyl, aryl, and inertly-substituted derivatives thereof.

2. A compound according to claim 1 which is a 1-aza-4,6-dioxabicyclo[3.3.0]octane compound corresponding to the formula:

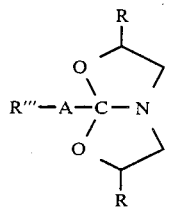

wherein

R''' and A are as previously defined; and

R is hydrogen or a substituent of up to 20 carbons selected from the group consisting of alkyl, aryl, and inertly substituted derivatives thereof.

3. The compound according to claim 1 wherein R''' is

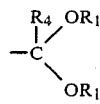

wherein $R_4$ is a $C_{1-10}$ group selected from alkyl and alkyl-terminated (poly)alkyleneoxy and each $R_1$ independently is $-CHR_2CH_2O-_nR_3$ where $R_2$ is hydrogen or methyl, $R_3$ is $C_{1-10}$ alkyl and n is a number greater than or equal to zero, or both $R_1$'s may be joined together to form a $C_{2-3}$ alkylene group.

4. The compound according to claim 2 wherein one or both of R are hydrogen or $C_{1-4}$ alkyl.

5. The compound according to claim 2 wherein one or both of R are methyl.

6. The compound according to claim 2 wherein A is $C_{2-4}$ alkylene.

7. The compound according to claim 2 which is selected from the group consisting of 5-(2-cyanobutyl)-3,7-dimethyl-1-aza-4,6-dioxabicyclo[3.3.0]octane; 5-(3-cyanobutyl)-3,7-dimethyl-1-aza-4,6-dioxabicyclo[3.3.0]octane; 5-(4-cyanobutyl)-3,7-dimethyl-1-aza-4,6-dioxabicyclo[3.3.0]octane; 5-(2-cyanobutyl)-3-methyl-1-aza-4,6-dioxabicyclo[3.3.0]octane; 5-(3-cyanobutyl)-3-methyl-1-aza-4,6-dioxabicyclo[3.3.0]octane; 5-(4-cyanobutyl)-3-methyl-1-aza-4,6-dioxabicyclo[3.3.0]octane; 5-(3,3-dimethoxypropyl)-3,7-dimethyl-1-aza-4,6-dioxabicyclo[3.3.0]octane; 5-(3,3-dimethoxypropyl)-3-methyl-1-aza-4,6-dioxabicyclo[3.3.0]octane; 5-(2-(1,3-dioxolanyl)ethyl)-3,7-dimethyl-1-aza-4,6-dioxabicyclo[3.3.0]octane; and 5-(2-(1,3-dioxolanyl)ethyl)-3-methyl-1-aza-4,6-dioxabicyclo[3.3.0]octane.

8. A process for preventing the deterioration of a functional fluid due to the presence of acid or water comprising adding to the functional fluid an amount effective to prevent the deterioration thereof of a bicyclic amide ketal corresponding to the formula:

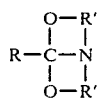

wherein R is hydrogen or a substituent of up to 20 carbons selected from the group consisting of alkyl, aryl and inertly-substituted derivatives thereof and R' each occurrence independently is a $C_{2-3}$ alkylene optionally substituted group with up to 4 R'' groups, where R'' is a substituent of up to 10 carbons selected from the group consisting of alkyl, aryl, and inertly-substituted derivatives thereof.

9. A process according to claim 8 wherein the bicyclic amide ketal derivative is present in the functional fluid in an amount from about 1 percent to about 90 percent based on the weight of base component.

10. A process according to claim 9 wherein the bicyclic amide ketal derivative is present in an amount from about 1.5 percent to about 50 percent.

11. A process according to claim 10 wherein the bicyclic amide ketal derivative is present in an amount from about 2 percent to about 25 percent by weight.

12. A process according to claim 8 wherein the bicyclic amide ketal is a 1-aza-4,6-dioxabicyclo[3.3.0]octane corresponding to the formula:

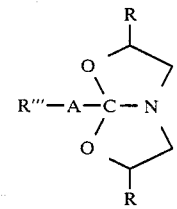

wherein

R''' is a nitrile, acetal or ketal group;

A is $C_{2-10}$ alkylene; and

R each occurrence independently is hydrogen or a substituent of up to 20 carbons selected from the group consisting of alkyl, aryl, and inertly-substituted derivatives thereof.

13. A process according to claim 12 wherein one or both of R are hydrogen or alkyl or aryl groups optionally inertly-substituted with nitrile, acetal, ketal, hydroxy, alkoxy, aryloxy, hydroxyalkyl, or hydroxy- or alkoxy-terminated (poly)alkyleneoxy.

14. A process according to claim 13 wherein acetal or ketal substituents correspond to the formula:

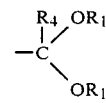

wherein $R_4$ is a $C_{1-10}$ group selected from alkyl or alkyl-terminated (poly)alkyleneoxy and each $R_1$ independently is $-CHR_2CH_2O-_nR_3$ where $R_2$ is hydrogen, methyl or ethyl, $R_3$ is $C_{1-10}$ alkyl and n is a number greater than or equal to zero, or both $R_1$'s may be joined together to form a $C_2$ or $C_3$ alkylene group.

15. A process according to claim 12 wherein one or both of R are hydrogen or $C_{1-4}$ alkyl.

16. A process according to claim 8 wherein the functional fluid comprises a nitrile functional acetal or ketal, an ester of a mono-, di- or polycarboxylic acid, a phosphoric acid ester, a silicone, a mineral oil, or a synthetic oil.

* * * * *